United States Patent [19]

Sherman et al.

[11] Patent Number: 4,994,466

[45] Date of Patent: Feb. 19, 1991

[54] METHOD OF TREATMENT FOR MULTIPLE SCLEROSIS

[75] Inventors: Fred P. Sherman, Hollywood; Elliot Hahn, North Miami Beach, both of Fla.

[73] Assignee: Baker Cummins Pharmaceuticals, Inc., Miami, Fla.

[21] Appl. No.: 537,589

[22] Filed: Jun. 14, 1990

[51] Int. Cl.$^5$ .............................................. A61K 31/44
[52] U.S. Cl. ..................................... 514/282; 514/903
[58] Field of Search .............................. 514/282, 903

[56] References Cited

U.S. PATENT DOCUMENTS 4,877,791 10/1989 Sherman ............................ 514/282
4,923,875 5/1990 Frost .................................. 514/282

OTHER PUBLICATIONS

Y. Olsson et al., *Acta Neurol. Scandinav.*, 50:611–618, (1974).
D. Johnson et al., *Ann. New York Acad. Sci.*, 1989, 727–728.
C. M. S. Fewtrell et al., *J. Physiol.*, 330:393–411, (1982).
S. K. Kostyk et al., *Brain Res.*, 504:284–288, (1989).
W. I. Rosenblum, *Brain Res.*, 49:75–82, (1973).
K. Sugiyama, *Nature*, 370:614–615, (1977).
G. N. Dietsch et al., *J. Immun.*, 142:1476–1481, (1989).
E. Orr, *Ann. New York Acad. Sci.*, 1989, 723–726.
Casale et al., *J. Aller. Clin. Immunol.*, 73:775–781, (1984).

*Primary Examiner*—Stanley J. Friedman
*Assistant Examiner*—Raymond J. Henley, III
*Attorney, Agent, or Firm*—Kirschstein, Ottinger, Israel & Schiffmiller

[57] ABSTRACT

A method of treating a patient suffering from multiple sclerosis comprising daily administration to such patient of from about 1 to about 100 mg of a pure narcotic antagonist, e.g., nalmefene or naltrexone. The antagonist may be administered in divided doses from one to four times daily, preferably by the oral route. Parenteral, transmucosal and transdermal administration may be utilized where suitable.

13 Claims, No Drawings

METHOD OF TREATMENT FOR MULTIPLE SCLEROSIS

BACKGROUND OF THE INVENTION

1. Field of the Invention

The invention relates to methods of treating multiple sclerosis.

2. Description of the Prior Art

Multiple sclerosis is a disorder of the central nervous system white matter characterized by local areas of inflammation, demyelination and gliosis. It is characterized by episodes of disorders of the optic nerves, spinal cord and brain which remit and recur over many years. This disease has a prevalence of 80 per 100,000 in Canada, Europe and the northern United States. Most cases have their onset in which individuals between 20 and 40 years of age. Most patients are eventually disabled by progressive paraplegia and/or ataxia.

Possible etiologies for multiple sclerosis include autoimmunity, viruses, free radical formation, mast cell mediation and the undecapeptide substance P which mediates augmented vascular permeability and vasodilation, possibly in a mast-cell dependent fashion. See J. E. Merrill et al., *J. Clin. Immun.*, 9: 84–89 (1989); M. Rodriguez, *Mayo Clin. Proc.*, 64: 570–576 (1989); E. Orr, *Ann. New York Acad. Sci.*, 1989, 723–726; S. K. Kostyk et al.; *Brain Res.*, 504: 284–288 (1989).

Studies suggest that mast cells participate in the pathophysiology of multiple sclerosis (Y. Olsson et al., *Acta Neurol. Scandinav.*, 50: 611–618 (1974)). The brain mast cells release vasoactive amines which may cause demyelination (D. Johnson et al., *Ann. New York Acad. Sci.*, 1989, 727–728). Also, these brain mast cells are in close proximity to peptidergic neurons which secrete neurotensin and substance P (C.M.S. Fewtrell et al., *J. Physiol.*, 330: 393–411 (1982)). Substance P not only is a potent mast cell stimulator but recently has been strongly implicated in the pathogenesis of multiple sclerosis plaques (S. K. Kostyk et al., supra). Histamine released from mast cells may alter blood vessel integrity and cause partial breakdown of the blood-brain barrier again implicated in the etiology of multiple sclerosis (W. I. Rosenblum, *Brain Res.*, 49: 75–82 (1973)). In addition, viral infection has been linked to multiple sclerosis and mast cells secrete with viral stimulation (K. Sugiyama, *Nature*, 370: 614–615 (1977)).

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570), sudden infant death syndrome (U.S. Pat. No. 4,639,455), autoimmune diseases (U.S. Pat. No. 4,857,533), arthritic and inflammatory diseases (U.S. Pat. No. 4,863,928), interstitial cystitis (U.S. Pat. No. 4,877,791), allergic rhinitis (U.S. Pat. No. 4,880,813) and mast cell-mediated dermatological disorders (U.S. Pat. No. 4,923,875).

Naltrexone (N-cyclopropylmethyl-14-hydroxydihydromorphinone) is another orally available narcotic antagonist with pure antagonist activity. Naltrexone has additionally been disclosed as useful for inducing anorexia (U.S. Pat. Nos. 4,477,457; 4,478,840) and for treating shock (U.S. Pat Nos. 4,267,182; 4,434,168).

In U.S. Pat. Nos. 4,877,791 and 4,923,875 it is disclosed that pure narcotic antagonists such as nalmefene and naltrexone may suppress histamine release from mast cells found in the bladder walls and the skin. Pure narcotic antagonists have not, however, been heretofore disclosed as having any utility in the treatment of multiple sclerosis or other neurodegenerative disorders.

There does not currently exist any modality of drug treatement for multiple sclerosis known to be safe and effective in a significant number of cases.

SUMMARY OF THE INVENTION

It is the object of the present invention to provide a method of treatment for multiple sclerosis which may achieve symptomatic relief, prevent recurrence of the symptomatic phase and induce remission. In keeping with this object and others which will become apparent hereinafter, the present invention resides in the daily administration to patients suffering from multiple sclerosis of from about 1 to about 100 milligrams of a pure narcotic antagonist, e.g., nalmefene or naltrexone. The oral route of administration is preferred for patient convenience, comfort and safety, but parenteral and other methods of administration may be utilized.

DETAILED DESCRIPTION OF THE INVENTION

The method of treatment of the present invention consists of the daily administration to patients suffering from multiple sclerosis of from about 1 to about 100 mg of a pure narcotic antagonist. As used herein, the term "pure narcotic antagonist" refers to substances which block or reverse the effects of exogenous or endogenous opioids or opiates while having no intrinsic narcotic agonist activity themselves.

The oral route of administration is preferred so that the patient can self-medicate safely and conveniently. A number of the pure narcotic antagonists, for example nalmefene and naltrexone, are highly effective and substantially bioavailable when administered orally. For purposes of the present invention, however, any of the pure narcotic antagonists may be administered parenterally or via other routes of administration as well (e.g., transmucosally), as long as adequate blood levels are achieved.

Any pure narcotic antagonist may be used in the method of the present invention, but not mixed agonist-antagonists. Such pure narcotic antagonists include, by way of example but not limitation, naloxone, nalmefene, naltrexone and diprenorphine. Preferred agents are those which are orally active and which have a long duration of action, in particular nalmefene and naltrexone.

In accordance with the present invention, the pure narcotic antagonist may be administered to patients suffering from multiple sclerosis in any conventional oral, parenteral, transmucosal, transdermal or other known dosage form. Oral dosage forms may include conventional tablets, capsules, caplets, pills, liquids and the like, including generally from about 0.5 to about 50.0 mg of the antagonist per dosage unit together with suitable, pharmaceutically-acceptable excipients, binders, sweeteners, coloring agents and other conventional additives.

Parenteral dosage forms may include conventional injectable solutions of the pure narcotic antagonists, for example, isotonic saline solutions, together with pharmaceutically acceptable buffers and preservatives. The parenteral dosage forms generally contain from about 0.5 to about 50.0 mg of antagonist per dosage unit and may be injected by the subcutaneous, intramuscular or intravenous routes.

Suitable transmucosal and transdermal dosage forms may include known sublingual, buccal and intranasal vehicles, as well as patches and topical vehicles containing penetrants which enhance transdermal absorption of the active antagonist ingredients. Examples of such transmucosal and transdermal vehicles may be found throughout the pharmaceutical literature, including in *Remington's Pharmaceutical Sciences,* 17th edition (1985).

By one preferred method, the pure narcotic antagonist may be initially administered to multiple sclerosis patients in two daily doses of about 0.5–5.0 mg each, for example for a one-week period, with gradual increments of about 1–3 mg b.i.d. up to a maximum of 50 mg. b.i.d.

In general, the method of the present invention is not dependent on any particular vehicle for the active narcotic antagonist agents or any particular route of administration. Any known method for getting effective treatment amounts of a pure narcotic antagonist into the bloodstream of the patient being treated for multiple sclerosis may be utilized.

Although there may be no need to administer the pure narcotic antagonists more than once or twice daily to achieve the results envisioned by the present invention, equally divided doses administered up to four times daily may be utilized. There have been few reports of any significant adverse effects with antagonists such as nalmefene or naltrexone at the dosage levels proposed by the present invention.

The following example provides an illustration of the method of the present invention. This example is not intended to limit or restrict the scope of the invention in any way, and should not be construed as providing dosage forms, regimens or methods of administration which must be utilized exclusively to practice the invention.

EXAMPLE

A patient diagnosed as suffering from multiple sclerosis is administered a 1.0 mg. tablet of nalmefene twice daily for 7 days, after which the dosage is increased in weekly increments of 1 mg b.i.d. until the patient is receiving 10–20 mg b.i.d. The patient may be maintained at that dosage level until his symptoms are stablized and remission of the disease process is observed.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

I claim:

1. A method of treating a patient suffering from multiple sclerosis comprising the daily administration to the patient of from about 1 to about 100 mg of a pure narcotic antagonist.

2. A method according to claim 1 wherein said antagonist is selected from the group consisting of naloxone, nalmefene, naltrexone and diprenorphine.

3. A method according to claim 1 wherein the antagonist is nalmefene or naltrexone.

4. A method according to claim 1 wherein the antagonist is administered to the patient orally.

5. A method according to claim 4 wherein the antagonist is administered to the patient in an oral dosage form comprising a tablet, capsule, caplet, pill or liquid containing from about 0.5 to about 50.0 mg of antagonist per unit.

6. A method according to claim 1 wherein the antagonist is administered to the patient parenterally.

7. A method according to claim 6 wherein the antagonist is administered to the patient by the subcutaneous, intramuscular or intravenous routes.

8. A method according to claim 1 wherein the antagonist is administered to the patient transmucosally or transdermally.

9. A method according to claim 1 wherein the antagonist is administered to the patient from one to four times daily.

10. A method according to claim 9 wherein the antagonist is administered to the patient from one to two times daily.

11. A method according to claim 10 wherein about 0.5 to about 5 mg of antagonist is administered to the patient twice daily for an initial period, after which the dosage amount is gradually increased to a maximum of 50 mg twice daily.

12. A method according to claim 10 wherein said antagonist is nalmefene.

13. A method according to claim 11 wherein about 1 mg of nalmefene is orally administered to the patient twice daily for an initial period of about seven days, after which the dosage is gradually increased to about 10–20 mg twice daily.

* * * * *